United States Patent
Boese et al.

(10) Patent No.: US 7,792,564 B2
(45) Date of Patent: Sep. 7, 2010

(54) DEVICE FOR DETERMINING THE RELATIVE POSITION OF A PLURALITY OF CATHETERS IN THE HUMAN BODY

(75) Inventors: Jan Boese, Eckental (DE); Martin Kleen, Furth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 1236 days.

(21) Appl. No.: 11/165,098

(22) Filed: Jun. 23, 2005

(65) Prior Publication Data
US 2006/0009754 A1    Jan. 12, 2006

(30) Foreign Application Priority Data
Jun. 25, 2004   (DE)   .................. 10 2004 030 834

(51) Int. Cl.
*A61B 5/04*   (2006.01)
*A61B 18/14*  (2006.01)
(52) U.S. Cl. .................. 600/374; 600/509; 600/41
(58) Field of Classification Search .................. 606/41; 600/374, 509
See application file for complete search history.

(56) References Cited

U.S. PATENT DOCUMENTS

| 6,749,606 | B2 * | 6/2004 | Keast et al. ................ 606/41 |
| 6,895,267 | B2 * | 5/2005 | Panescu et al. ............. 600/424 |
| 2002/0115941 | A1 | 8/2002 | Whayne et al. |
| 2003/0199864 | A1 * | 10/2003 | Eick .......................... 606/41 |

FOREIGN PATENT DOCUMENTS

| EP | 1 502 555 A1 | 2/2005 |
| GB | 2 388 196 A | 11/2003 |

* cited by examiner

*Primary Examiner*—Lee S Cohen

(57) ABSTRACT

Device for determining the relative position of two or more catheters in the human body, there being disposed on each catheter (4, 5), preferably in the area of the catheter tip, at least one measuring electrode (ME1-ME8; ME9, ME10) which can be connected to a voltage source together with one or more measuring electrodes of a further catheter, wherein the resistance between the measuring electrodes, and hence the distance of the measuring electrodes, can be determined via a current measurement.

10 Claims, 3 Drawing Sheets

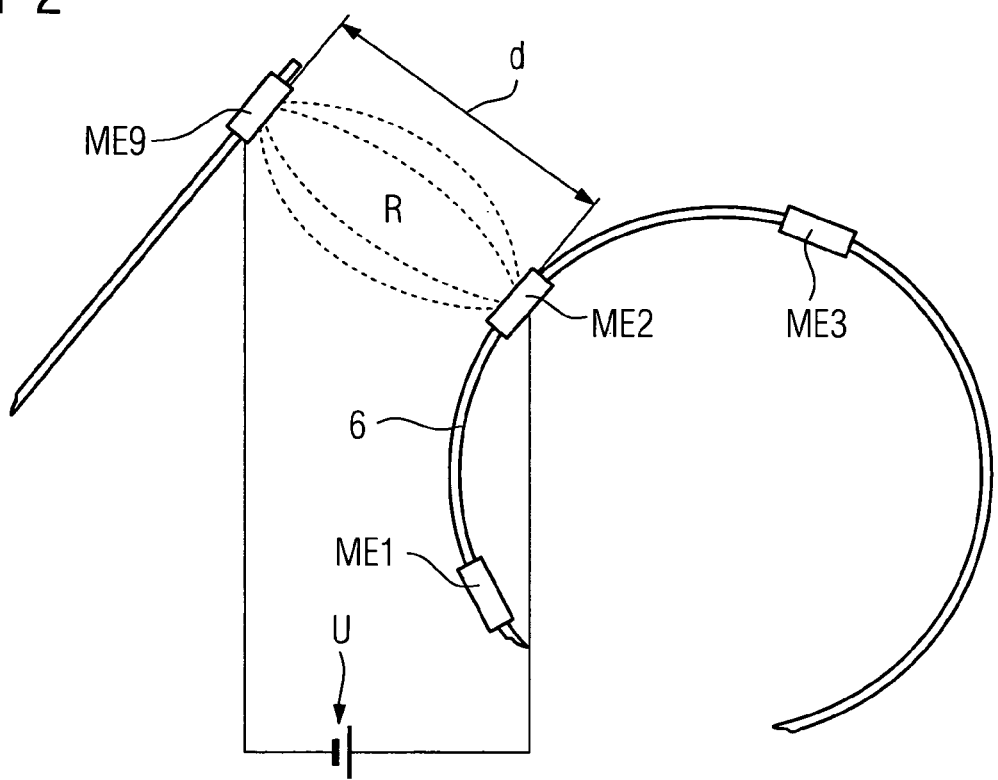
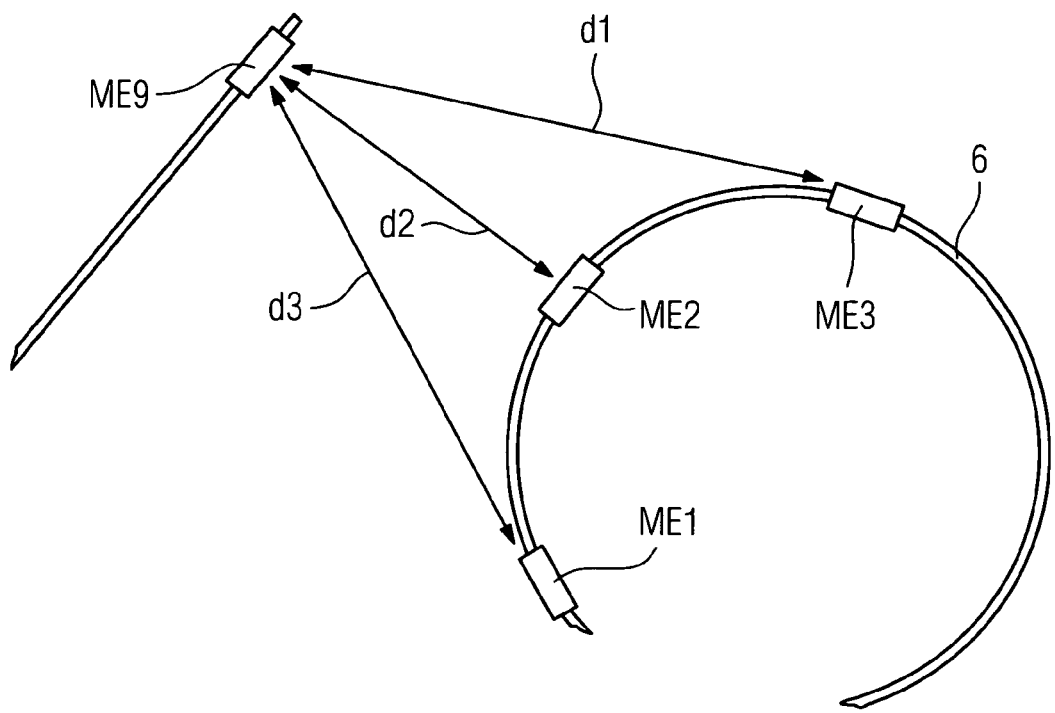

DEVICE FOR DETERMINING THE RELATIVE POSITION OF A PLURALITY OF CATHETERS IN THE HUMAN BODY

CROSS REFERENCE TO RELATED APPLICATIONS

This application claims priority to the German application No. 10 2004 030 834.9, filed Jun. 25, 2004 which is incorporated by reference herein in its entirety.

FIELD OF INVENTION

The invention relates to a device for determining a relative position of catheters inserted into a human body.

BACKGROUND OF INVENTION

In cardiology, more particularly electrophysiology, two or more catheters are introduced through the vascular system into the heart in order to carry out diagnosis and/or therapy therein. Since relatively large spaces are present in the heart compared to the vessels, the problem arises of navigating the catheters accurately to the desired destination in these spaces and to keep track of their location. In certain cases it is necessary to determine the exact position of a catheter in the space with absolute precision, for example in order to use said position for imaging representations.

SUMMARY OF INVENTION

Until now, a method measuring absolutely in the 3D space has been used in order to determine the positions of intracardiac catheters relative to one another. Thus, for example, Biosense Webster's Carto positioning system uses an electromagnetic field in which catheters equipped with coils are moved. It is complicated, time-consuming and expensive to set up, calibrate and operate said system. However, systems measuring absolutely are by no means essential for those cases in which only the position of two or more catheters relative to one another is required, in other words, for example, for electrophysiological examinations using what is known as a lasso catheter, with the result that the high technical and financial outlay is not justified.

An object of the invention is therefore to create a device for determining the relative position of two or more catheters in the human body, said device being simple in design and easy to operate so that it can be used without difficulty by anyone with the ability to carry out investigations by means of catheters in the human body.

This object is achieved by the claims.

Since the blood in which the catheters are located is electrically conducting, a current flows between the measuring electrodes. A resistance is calculated from the known voltage and the measured current. The resistance is proportional to the volume of blood that the current has flown through, in other words, therefore, the distance between the two electrodes. Moreover, blood can vary slightly in terms of its composition and consequently the conductivity can also increase or decrease. However, as said variations are minor and there is a constant strong bloodstream in the heart, the variations will barely register given appropriate averaging. For illustration purposes it should be pointed out that while the body is at rest approx. 4-5 liters of blood per minute flow constantly through the atria and ventricles.

In order to avoid disruptions to the current measurement due to signals generated in the body itself or to external electrical signals, an alternating voltage having a specific phase and frequency is preferably applied to the electrodes. The current flowing through the electrodes is measured on a phase- and frequency-selective basis, so only the applied voltage is taken into account in the calculation of the resistance and other voltages are largely suppressed.

A measuring electrode in one catheter will be closer to a measuring electrode of the other catheter than another measuring electrode, which means that the resistance of the blood between the dynamically connected pair of electrodes is therefore greater in the first case than in the second case. By systematic switching of the voltage between all possible pairings of the measuring electrodes of the different catheters with the aid of a control unit, or alternatively by applying voltages of different frequency or at least of different frequency coding to the different electrode pairings, it is thus possible to deduce the spatial position of one catheter relative to the other catheter.

The distance and the relative position can be fed back to the user via pitch coding, for example. Thus, the sound could be at its deepest (or softest) when the distance from the electrode on one catheter to all the electrodes on the other catheter is at its smallest. In another switchable mode the desired position at the edge of the second catheter can be indicated by corresponding sound coding.

In a development of the invention a calibration and calculation of the absolute distance can be performed if the voltage is applied between two measuring electrodes of one catheter that have a known distance relative to one another. Since the material of the catheter itself insulates, only the conductivity of the blood can determine the resistance. Thus, the ratio of length of the current path in the blood and distance can be determined.

In this way the feedback to the user (e.g. by means of pitch coding) can be effected with even greater precision. By means of a pictogram it is possible, taking into account the relativity of the measurement in relation to the position of the heart, to represent the absolute position and distance of the catheters relative to one another.

With particular advantage one of the catheters can be what is known as a lasso catheter, that is to say a catheter having a ring-shaped configuration at the end, which, after being introduced into the cardiac ventricle, deforms into this annular shape due to the elastic property of the material, whereby with such a lasso catheter a plurality of measuring electrodes disposed equidistantly in a distributed arrangement around the loop can be provided, while the second catheter can be an intervention catheter, in particular an ablation catheter.

A lasso catheter of said type is introduced into the junction of a large vessel which leads into the cardiac ventricle (pulmonary vein) and even without use of a navigation system is equipped with a number of electrodes for deriving intracardiac potential s. Owing to the ring shape, that is to say on account of the loop which forms at the front end, it is possible to deduce the position and direction of the potentials in the vessel toward the heart. The straight intervention catheter can be navigated precisely to these sites of potential derivation by the electrophysiologist with the aid of the lasso catheter in order possibly to ablate aberrant conduction pathways with current. In an embodiment of the invention the electrodes which are required in any case for electrophysiological purposes can be used at the same time for the purposes of navigation and determination of the relative position of the catheters; in other words, the electrodes of the catheters for the electrophysiology can also simultaneously be the measuring electrodes. It would also, of course, be possible to use separate electrodes as measuring electrodes.

BRIEF DESCRIPTION OF THE DRAWINGS

Further advantages, features and details of the invention will emerge from the following description of an exemplary embodiment as well as with reference to the drawings, in which:

FIG. 2 shows an enlarged representation of the loop of the lasso catheter and the tip of the ablation catheter with the electrodes, to which a voltage source can be applied pair by pair in alternation.

FIG. 3 shows a representation corresponding to FIG. 2 in which the different distances between an electrode of the ablation catheter and the different electrodes of the lasso catheter are indicated.

DETAILED DESCRIPTION OF NVENTION

Figure 1:
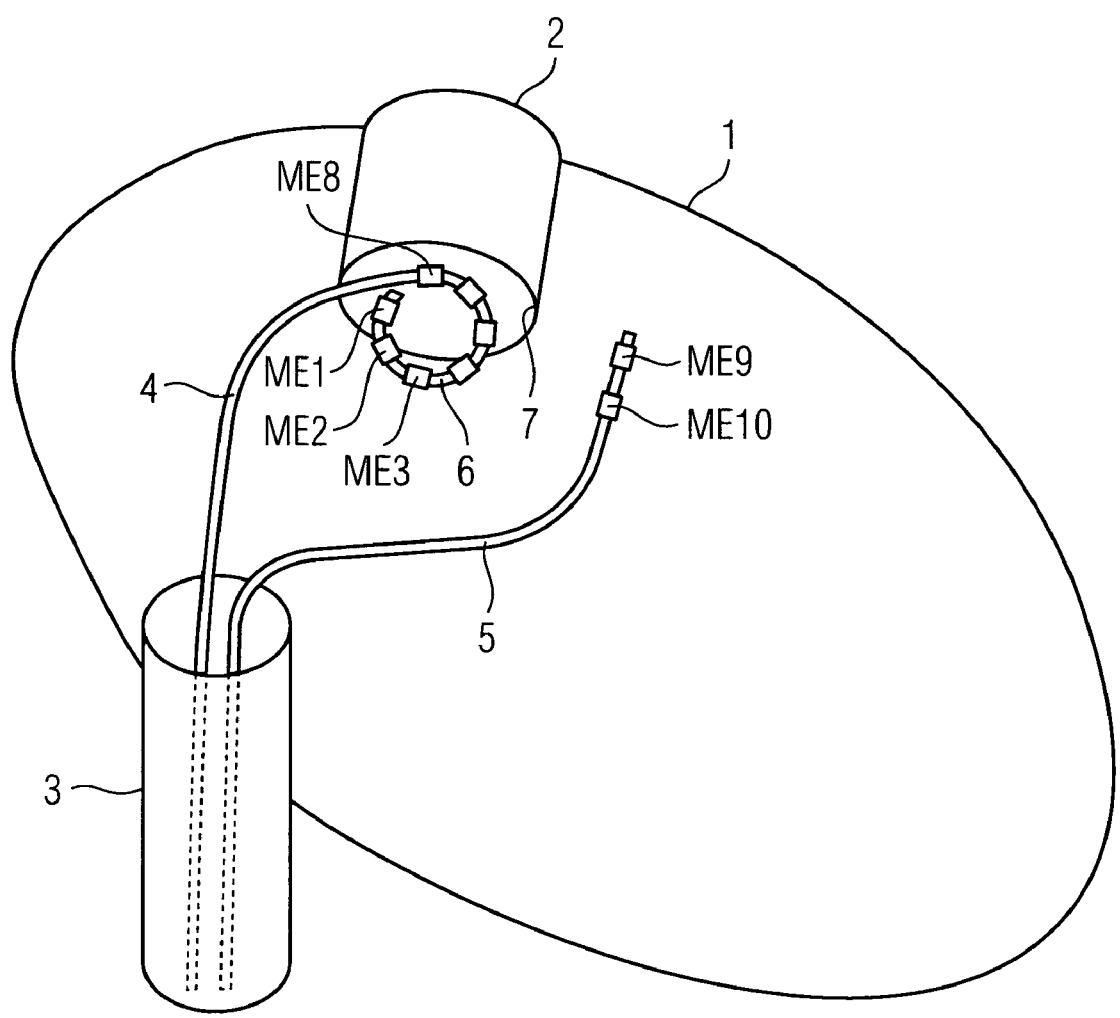
FIG. 1 shows a schematic representation of a cardiac ventricle as well as a lasso catheter and an ablation catheter which is to be navigated with the aid of the relative position determining device according to the invention.

The reference numeral 1 in FIG. 1 denotes a schematically indicated cardiac ventricle with a confluent pulmonary vein 2 and a further hollow vein (vena cava) 3 through which a lasso catheter 4 and a straight intervention catheter (ablation catheter) 5 can be introduced.

At its front end the lasso catheter 4 has a loop 6 which forms in the heart owing to the elastic property of the material and which is equipped with a plurality of measuring electrodes ME1 to ME8. In the same way two measuring electrodes are likewise arranged at the front end of the straight intervention catheter. The measuring electrodes ME1 to ME8 are the electrodes on the lasso catheter which are required in any case for electrophysiological purposes and are used as well solely for the inventive device for determining the relative position of the two catheters. In a similar manner the electrode ME9 on the straight catheter is the intervention electrode for ablating the aberrant conduction pathways in the junction aperture of the pulmonary vein and only the electrode ME10, which otherwise is by no means absolutely essential for normal application cases, would represent an additional electrode which is required only for the inventive device for determining the relative position of the catheters.

In FIG. 2 it is indicated how, by application of a voltage U to the electrode ME9 on the one hand and one of the electrodes, in this case specifically ME2, of the loop 6 of the lasso catheter on the other hand, a current flow is produced from which a resistance R can be calculated which in turn is proportional to the distance between the electrodes ME9 and ME2 affected in each case.

It can be seen in FIG. 3 that each distance d1 to d3 spans open a sphere in the space, on which sphere the electrode ME9 can be located. The point of intersection or space of intersection of a number of such spheres indicates the position of the electrode ME9 relative to the lasso catheter with the electrodes ME1 to ME8 (for better clarity only three are shown in FIG. 3). The more measuring electrodes the lasso catheter has, the more accurate will be the measurement. If a further electrode ME10 is attached to the straight intervention catheter 5 with the electrode ME9, the accuracy increases given the known distance of said electrode and the orientation of said catheter in the space can be calculated.

Figure 4:
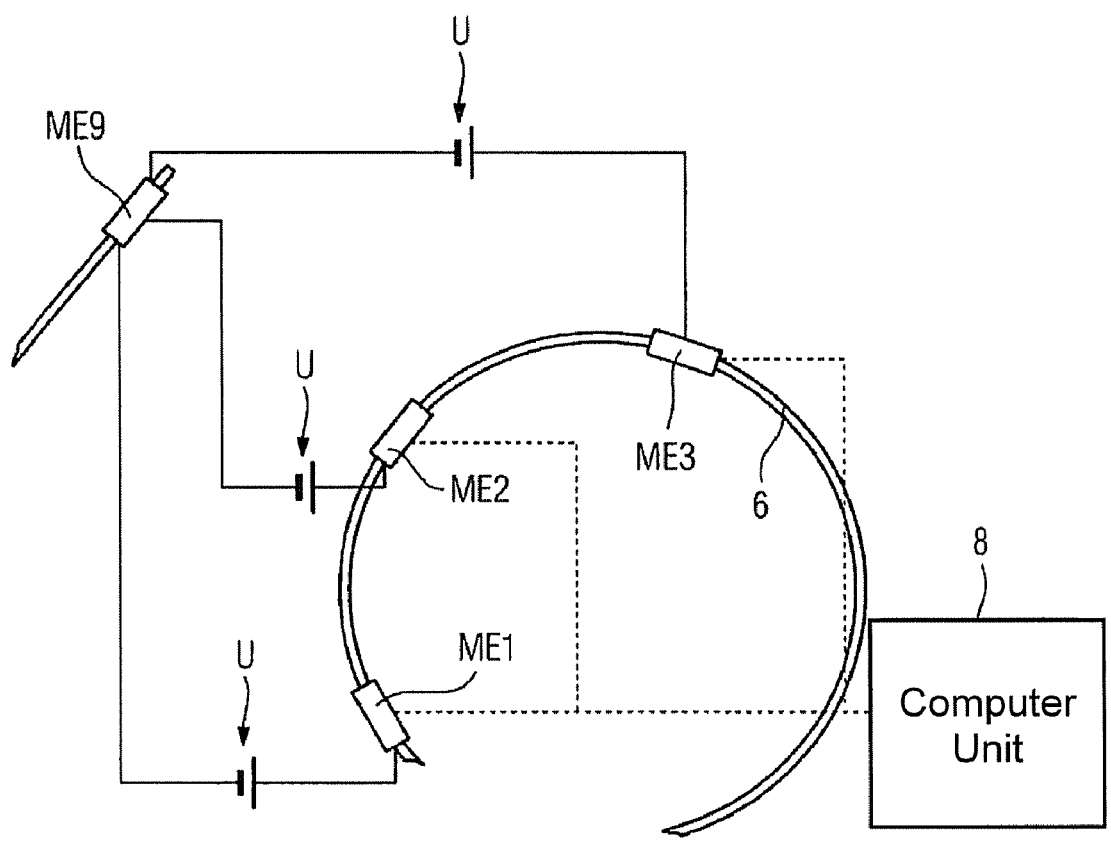
FIG. 4 shows a representation corresponding to FIGS. 2 and 3 with an indicated computer unit for switching between the different measuring electrode pairs.

In FIG. 4 a computer unit 8 controls a single voltage source which can be applied in rapid alternation to different pairs of measuring electrodes in order to determine, from the current values measured in each case, the distance by way of the resistance. The result can be output either by means of pitch coding or with the aid of pictograms.

The invention claimed is:

1. A device for determining the relative position with respect to one another of a first catheter and a second catheter in a human body, comprising:
    a first measuring electrode arranged on the first catheter;
    a second measuring electrode arranged on the second catheter;
    a power supply unit connected to the first and second measuring electrodes;
    a number of additional measuring electrodes arranged on at least one of the first and second catheters, said additional number of measuring electrodes connected to the power supply unit;
    a control unit configured to selectively and dynamically form at least two different pairs of measuring electrodes when said additional number of measuring electrodes is operatively combined at different times with the first measuring electrode, or with the second measuring electrode, or with at least some of said additional number of electrodes, wherein each of said at least two different pairs of electrodes consists of one measuring electrode positioned on the first catheter and another measuring electrode positioned on the second catheter; and
    a measuring unit for determining respective electrical resistances between each of said at least two different measuring pairs of measuring electrodes by measuring respective electrical currents flowing through said at least two different measuring pairs of measuring electrodes and for determining respective distances, the determined distances being sufficiently large to encompass a chamber of a human heart where the device is introduced to measure different spacing separations between each of said at least two different measuring pairs of measuring electrodes based on the determined electrical resistances, wherein the relative position of the first catheter with respect to the second catheter is determined using the determined distances.

2. The device as claimed in claim 1, wherein the first electrode is arranged at a tip of the first catheter.

3. The device as claimed in claim 1, wherein the power supply unit includes at least a first and a second alternating voltage power supply having different frequencies, and the electrical current is measured by a current measuring instrument configured to measure such currents having a specific frequency and/or a specific phase.

4. The device as claimed in claim 1, wherein the first electrode has a known distance from another electrode arranged on the first catheter, the power supply unit is connected to the first electrode and said another electrode, and a flow of electrical current between the first electrode and said another electrode is measured for calibrating the measuring unit with regard to a measurement of an absolute distance.

5. The device as claimed in claim 1, wherein the first or the second catheter is a lasso catheter having a number of measuring electrodes arranged equidistantly on and distributed over a loop of the lasso catheter.

6. The device as claimed in claim 1, wherein the first or the second catheter is an intervention catheter.

7. The device as claimed in claim 6, wherein the intervention catheter is an ablation catheter.

8. The device as claimed in claim 1, wherein the measuring unit is configured to output the determined distance and relative position to a user of the device using an acoustical signal having a signal frequency related to the determined distance and/or relative position.

9. The device as claimed in claim 1, wherein the measuring unit is configured to output the determined distance and relative position to a user of the device using a pictogram.

10. The device as claimed in claim 1, wherein the first electrode is included in a working electrode of the first catheter, the working electrode configured to execute a medical examination and/or treatment procedure.

* * * * *